United States Patent
Simoni et al.

(10) Patent No.: US 8,279,427 B2
(45) Date of Patent: Oct. 2, 2012

(54) METHOD AND APPARATUS FOR MEASURING THE REFRACTIVE INDEX OF A MATERIAL WITH BRAGG GRATINGS

(75) Inventors: Francesco Simoni, Rome (IT);
Riccardo Castagna, Fermo (IT);
Luigino Criante, Montegiorgio (IT);
Daniele Eugenio Lucchetta, Jesi (IT);
Francesco Vita, Sant'Anastasia (IT)

(73) Assignee: Universita Politechnica delle Marche, Ancona (IT)

( * ) Notice: Subject to any disclaimer, the term of this patent is extended or adjusted under 35 U.S.C. 154(b) by 270 days.

(21) Appl. No.: 12/596,552

(22) PCT Filed: Apr. 17, 2008

(86) PCT No.: PCT/IT2008/000257
§ 371 (c)(1),
(2), (4) Date: Jan. 13, 2010

(87) PCT Pub. No.: WO2008/129580
PCT Pub. Date: Oct. 30, 2008

(65) Prior Publication Data
US 2010/0110429 A1    May 6, 2010

(30) Foreign Application Priority Data

Apr. 18, 2007 (IT) .............................. AN2007A0019

(51) Int. Cl.
*G01N 21/41* (2006.01)
(52) U.S. Cl. .......................... 356/128; 356/326; 356/328
(58) Field of Classification Search .................. 356/128, 356/326, 328
See application file for complete search history.

(56) References Cited

U.S. PATENT DOCUMENTS

| | | | |
|---|---|---|---|
| 4,436,420 A * | 3/1984 | Depp et al. ..................... | 356/128 |
| 5,071,248 A * | 12/1991 | Tiefenthaler et al. ......... | 356/128 |
| 5,502,560 A | 3/1996 | Anderson et al. | |
| 5,615,008 A * | 3/1997 | Stachelek ...................... | 356/301 |
| 6,844,206 B1 | 1/2005 | Phan et al. | |
| 7,184,135 B2 | 2/2007 | Laffont et al. | |
| 7,301,628 B2 * | 11/2007 | Cunningham et al. ......... | 356/326 |
| 7,541,573 B2 * | 6/2009 | Emmerson et al. ......... | 250/227.18 |
| 2008/0129985 A1 * | 6/2008 | Laffont et al. ................. | 356/128 |

FOREIGN PATENT DOCUMENTS

GB    2 141 223 A    12/1984

OTHER PUBLICATIONS

International Search Report, dated Oct. 24, 2008, from corresponding PCT application. Francesco Vita et al., "Detailed investigation of high-resolution reflection gratings through angular-selectivity measurements", Journal of Optical Society of America B, Mar. 2007, pp. 471-476, vol. 24, No. 3, Optical Society of America, XP-002499716.

* cited by examiner

*Primary Examiner* — Layla Lauchman
(74) *Attorney, Agent, or Firm* — Young & Thompson

(57) ABSTRACT

A method for measuring the refractive index of a material with Bragg gratings includes the emission of a collimated radiation beam (9) from a radiation source (4) with a large spectrum and orientation thereof along a direction normal to the material (2) to be examined, the propagation of the collimated radiation beam (9) entering the material (2), then a Bragg diffraction grating (3) that is obliquely placed to the direction of the collimated radiation beam (9), and again the material (2), the subjection to spectral analysis of the collimated radiation beam exiting the material (2), the grating (3) producing a minimum in the spectrum subjected to the spectral analysis in accordance with Bragg's law, and the calculation of the refractive index of the material (2) from the measure of the wavelength corresponding to the minimum in thus spectrum. A relevant apparatus is described.

20 Claims, 3 Drawing Sheets

METHOD AND APPARATUS FOR MEASURING THE REFRACTIVE INDEX OF A MATERIAL WITH BRAGG GRATINGS

TECHNICAL FIELD

This invention relates to a method and apparatus for measuring the refractive index of a material with Bragg gratings. Further the invention concerns an apparatus for performing this method.

BACKGROUND ART

Refractometers are used for measuring the refractive index of a material or other physical or chemical properties thereof, that are somehow related to the refractive index. Some of the existing refractometers are based on Bragg diffraction gratings, such as those described in the U.S. Pat. No. 7,184,135 granted on Feb. 27, 2007, and the International Patent Application WO 2006/061543 published on Jun. 15, 2006, the Commissariat a l'Energie Atomique of Paris (France) being the owner thereof. The refractometers therein disclosed use an optical fibre. In the fibre core there is a Bragg diffraction grating, having planes not at right angle with the axis of the fibre. When light propagating through the fibre is incident on the grating a diffracted light is coupled in part to the discrete spectrum of the counter-propagating cladding modes, in part to the continuum of radiative modes sending energy outside the fibre. The diffracted light spreads out in different way between the cladding modes and the radiative modes depending on the refractive index of the medium i.e. the material to be examined in which the fibre is dipped.

According to the U.S. Pat. No. 7,184,135 the measure of the refractive index is obtained by the spectral analysis of the cladding modes to be performed by a very high resolution spectrometer. According to the Patent Application WO 2006/061543, the refractive index is determined by a measure of power which is uncoupled from the fibre by means of the radiative modes. Thus, both methods are based on a physical principle according to which the refractive index influences the value of the effective index of the cladding and radiative modes, and then on how the light diffracted is spread out between such modes. In the methods of the above cited documents an important role in determining the resolution and the measuring range of the instrument is played by values of refractive index of the fibre, which are practically not modifiable, as well as by parameters of the grating. This limits a lot the flexibility of using the described methods.

Further, it should be pointed out that the above described methods achieve high resolutions only with extremely expensive instruments, which are allowable only in optical laboratories. In fact, the method of the above US patent requests a spectrometer having a resolution in the region of a picometer, and the method according to the above International Patent Application needs a sensor and electronics component part, both being able to operate with very unfavourable signal-to-noise ratios.

SUMMARY OF THE INVENTION

Although the present invention is based on the use of a Bragg grating like the above cited patents, it is founded on a different operation principle that allows some limitations of the above said inventions to be overcome, as well as provides several other advantages, as described below.

In particular, an object of the present invention is to provide method for measuring the refractive index that is based on a physical principle which is simple and dependent on a low number of parameters.

Another object of the invention is to allow measures of the refractive index at different wavelengths with the same resolution being maintained and one large spectrum source being used.

Further an object of the invention is to provide a method of measuring a refractive index without any need of using optical fibres so that on one hand it can be used together with common spectrophotometers, and on the other hand error components that are inevitably associated to imperfections and mechanical distortions of the fibre can be eliminated.

Therefore, according to a first aspect of the invention there is provided a method for measuring the refractive index of a material with Bragg gratings.

According to a second aspect of the invention there is provided a relevant apparatus.

The invention has several advantages. The method is extremely simple and the apparatus is cheap and versatile. In particular, its main advantage is the possibility to transform any commercial spectrometer into a precise and simple refractometer by using only a cuvette containing a Bragg diffraction grating. Such a fitting in addition to be extremely cheap allows real-time measures to be performed in a fluid of any kind, provided that it is sufficiently transparent, also in flow conditions. Further, the apparatus is fit to measure changes of refractive index in specimens that are subjected to external modifications. This possibility is, for example, very interesting to study and monitor chemical, biological electro- or photo-induced reactions, etc. The method is inherently fit to measure a refractive index in a large frequency range from ultraviolet to microwaves, simply by utilising a suitable diffraction grating. Inside each spectral range, measures of refractive index at different wavelengths can be easily obtained by permitting the grating to be rotated inside the cuvette.

BRIEF DESCRIPTION OF DRAWINGS

The principle of operation and the main characteristics of the present invention can be better understood from a detailed description of two embodiments thereof with reference to the enclosed drawings, wherein.

DESCRIPTION OF EMBODIMENTS OF THE INVENTION

An apparatus for embodying the method of measuring the refractive index of a material is described below in two embodiments thereof.

Figure 1:
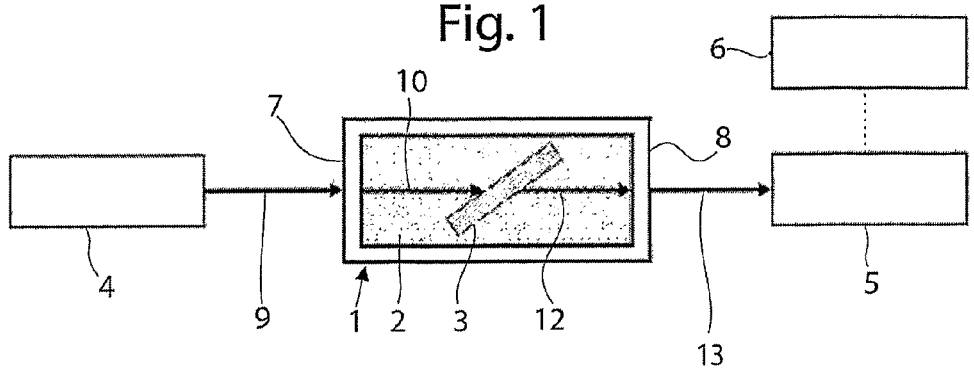
FIG. 1 is a block diagram generally representing an apparatus for measuring the refractive index of a material by using Bragg gratings according to a first embodiment of the present invention, when the material to be examined is fluid.

Referring to FIG. 1, which is a block diagram generally representing an apparatus in a first embodiment thereof, in a cuvette 1 there is placed a material 2 to be examined, that can be contained therein, for example a liquid, a gel, a suspension, etc. A Bragg diffraction grating, which is mounted inside the cuvette 1, is indicated as 3. A radiation source emitting a radiation beam with a large spectrum, operating in the wavelength range of interest is indicated as 4, a spectrometer adapted to collect and analyse the spectrum of the radiation beam exiting the cuvette is indicated as 5 and calculating means to calculate the refractive index is indicated as 6.

The cuvette 1 has a couple of opposite walls operating as an entrance window 7 and an exit window 8, respectively, for the radiation beam. The entrance and exit windows 7, 8 are parallel and transparent in the wavelength range of interest.

The Bragg diffraction grating 3, which is mounted inside the cuvette 1, is obliquely oriented to the entrance and exit windows 7, 8.

The method of measuring the refractive index according to the invention can be represented as follows.

A collimated, entering radiation beam, which is represented by an arrow 9, is emitted by the radiation source 4 and strikes perpendicularly the entrance window 7 of the cuvette 1. The radiation beam propagates (arrow 10) through the material 2 to be examined contained in the cuvette 1, then through the Bragg diffraction grating 3 (arrow 11 in FIG. 2, which is an enlargement of a part in FIG. 1) and then again through the material 2 to be examined (arrow 12), before exiting the cuvette through the exit window 8, in an exiting radiation beam 13.

The exiting radiation beam 13 is collected by the spectrometer 5.

The spectrometer 5, with the calculating means 6, provides a measure of the wavelength diffracted by the grating. Being known this wavelength, the refractive index of the material 2 to be examined, contained in the cuvette 1, can be calculated.

A first embodiment of the apparatus is described below.

A cuvette 1 having a parallelepiped shape, usually made of glass or quartz, is used to contain the material 2 to be examined, generally a liquid. If the material to be examined is aeriform, the cuvette should be sealed. Two opposite walls of the cuvette 1, being parallel to each other and transparent in the wavelength range of interest, act as windows 7, 8 for the entrance and the exit of the radiation beam.

The Bragg diffraction grating 3, usually a phase grating, is placed in the cuvette 1, being obliquely oriented to the entrance window 7 and the exit window 8, and in contact with the fluid to be examined on both sides thereof.

The collimated radiation beam 9, which is emitted by the radiation beam 4 with large spectrum, usually a lamp, strikes the cuvette 1 perpendicularly to the entrance window 7, then it propagates as a beam 10 in the material 2 to be examined without undergoing dispersion.

Figure 2:
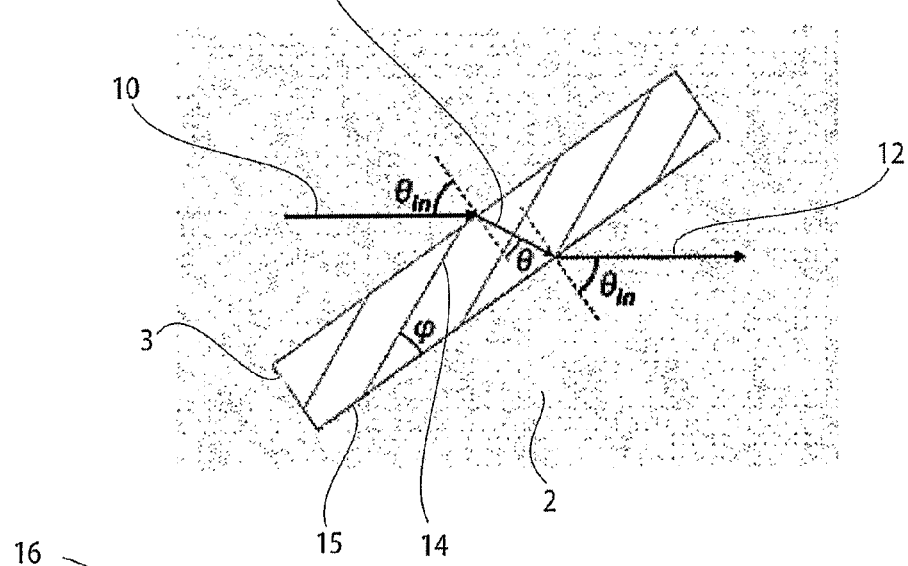
FIG. 2 is an enlarged detail of a part in FIG. 1.

At the first interface between the material to be examined and the grating 3 the beam 10 is refracted according to Snell's law $$n \sin \theta_{in} = n_0 \sin \theta, \qquad (1)$$

wherein $n_0$ is the mean refractive index of the grating, n the refractive index of the material to be examined, $\theta_{in}$ and $\theta$ are the propagation angle in the material and in the grating respectively, both being measured with respect to the normal to the grating, as shown in detail in FIG. 2.

For a given propagation angle $\theta$ of the beam inside the grating a particular wavelength $\lambda$ is diffracted laterally, in accordance with the Bragg's law $$\lambda = 2\Lambda n_0 \cos(\theta - \phi), \qquad (2)$$

wherein $\Lambda$ is the pitch of the grating 3 and $\phi$ the inclination angle of the reticular planes generally indicated as 14, i.e. the angle between the reticular planes 14 and the external surface 15 of the grating. On the contrary, all wavelengths that do not meet Equation 2 do not undergo diffraction, cross the grating 3 without being deviated, then again the surrounding material to be examined, to exit the cuvette as indicated in 12 through the exit window 8.

The beam 13, exiting the cuvette 1 and containing all wavelengths not diffracted by the grating 3, is collected and analysed by the spectrometer 5 operating in the wavelengths of interest. From what above said the transmission spectrum acquired by the spectrometer will show a minimum in correspondence of the Bragg wavelength diffracted by the grating. From the measure of such a value, by combining Snell's law and Bragg's law (Equation 1 and 2), it is possible to calculate the refractive index of the material to be examined in block 6.

Figure 3:
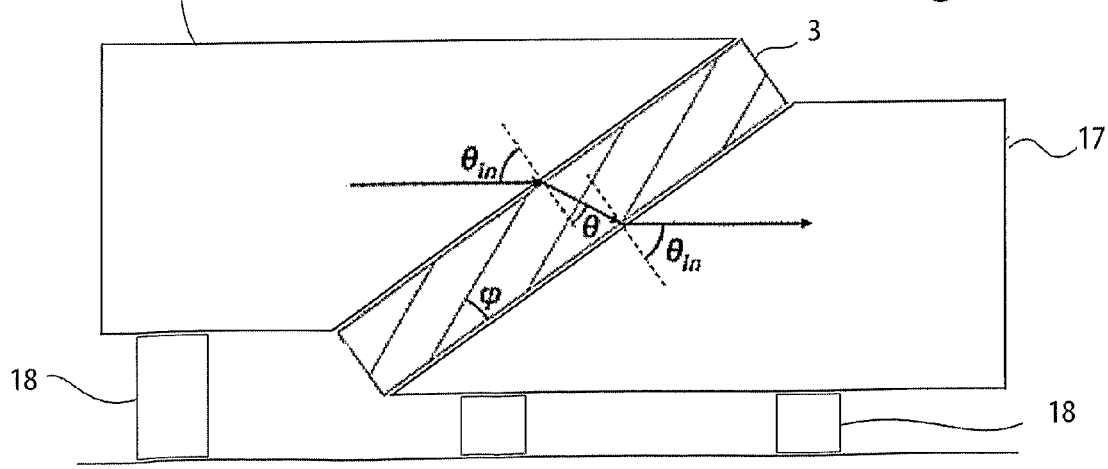
FIG. 3 is an enlarged detail, similar to that in FIG. 2, of a second embodiment of the apparatus for a transparent solid material to be examined.

With reference to FIG. 3, which is an enlarged detail, similar to that in FIG. 2, of the apparatus in FIG. 1, a second embodiment thereof is shown. Therein, when the material to be examined is a transparent solid, a Bragg grating is indicated again as 3, and prismatic bodies 16, 17 of the same material to be examined, which are placed in contact with the grating 3, are crossed by the same radiation beam coming from a source 4 (not shown). The prismatic bodies 16, 17 have opposed faces which are complementary inclined, between which the Bragg diffraction grating is interposed similarly inclined. In FIG. 3 supporting means sustaining the prismatic bodies and the Bragg grating are represented with 18.

This arrangement allows the calculation of the refractive index of the solid material to be examined by the same method according to the invention as utilised for the fluid material.

With respect to the most of the traditional refractometers that determine the refractive index through angular measures, the apparatus according to the invention transduces variations of $\theta$ depending on the refractive index n into variations of the diffracted wavelength $\lambda$ which are easily measurable with high sensitivity by commercial spectrometers.

The achievable sensitivity can be evaluated as follows. The combination of Snell's law and Bragg's law (Equations 1 and 2) provides the response curve of the apparatus, i.e. the pattern of the wavelength $\lambda$ diffracted by the Bragg grating in dependence on the refractive index n of the material to be examined:

$$\lambda = 2n_0 \Lambda \cos\left[\varphi - \arcsin\left(\frac{n \sin\theta_{in}}{n_0}\right)\right]. \qquad (3)$$

By differentiating with respect to n, the sensitivity S of the apparatus is obtained:

$$S = \frac{d\lambda}{dn} = 2\Lambda n_0 \sin\left[\varphi - \arcsin\left(\frac{n\sin\theta_{in}}{n_0}\right)\right] \frac{\sin\theta_{in}}{\sqrt{n_0^2 - n^2\sin^2\theta_{in}}}, \quad (4)$$

that can be also interpreted as a product of $$S_1 = \frac{d\lambda}{dn} = 2n_0\Lambda\sin\left[\varphi - \arcsin\left(\frac{n\sin\theta_{in}}{n_0}\right)\right] \quad (5)$$

and $$S_2 = \frac{d\theta}{dn} = \frac{\sin\theta_{in}}{\sqrt{n_0^2 - n^2\sin^2\theta_{in}}}, \quad (6)$$

the first one being obtained by differentiating Bragg's law, the second one by differentiating Snell's law.

By suitably choosing the grating parameters $\Lambda$, $\theta_{in}$ and $\varphi$, ($n_0$ is generally fixed by the choice of the grating material) the sensitivity of the apparatus can be maximised in the wavelength range of interest.

Figure 4:
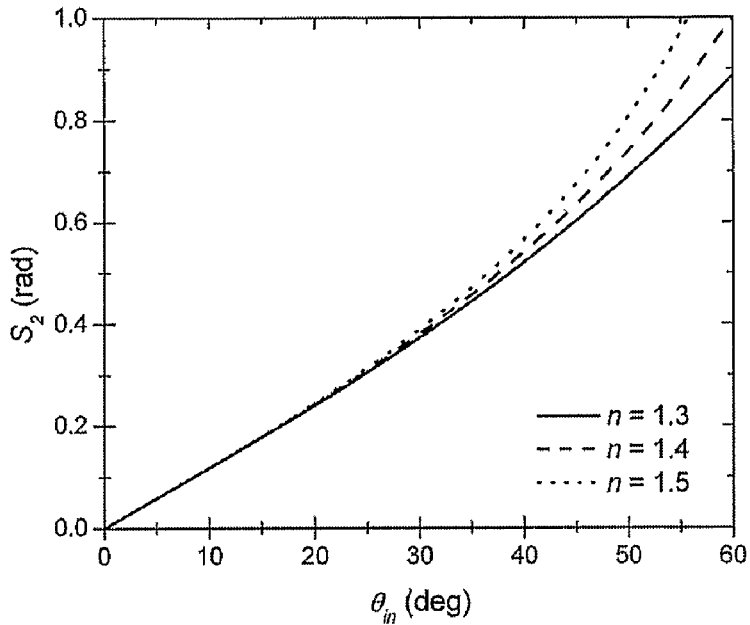
FIG. 4 is a graphic of a quantity $S_2$, as defined by Equation 6, being expressed in radians in ordinate, depending on the incidence angle $\theta_{in}$, being expressed in degrees in abscissa, for $n_0=1.49$ and different values of n.

On the base of Equation 6, $S_2$ depends only from $\theta_{in}$; its typical pattern is shown in FIG. 4 for $n_0=1.49$ and different values of n. As $S_2$ increases monotonically with $\theta_{in}$, it is suitable to choose the value as great as possible for the incidence angle; reasonable values are about 50÷60°, corresponding to $S_2 \approx 0.7 \div 1.0$ radian.

According to Equation 5, $S_1$ increases linearly with $\Lambda$; for a given $\Lambda$, $S_1$ is in any case maximum when the argument of sinus tends to $\pi/2$, i.e. when $\varphi-\theta \approx \pi/2$, wherein $$\theta = \arcsin\frac{n\sin\theta_{in}}{n_0}$$

is the propagation angle of the beam in the grating according to Equation 1. From a physical point of view this means that $S_1$ is maximum when the direction of the beam propagation in the grating is approximately parallel to the reticular planes. In this situation $S_1 \approx 2n_0 \Lambda \approx 3\Lambda$ (normally $n_0 \approx 1.5$), that multiplied for a value of 0.8÷0.9 for $S_2$, results in a whole sensitivity $S \approx 2.5\Lambda$.

A range of operation of the apparatus must be also considered in the choice of the grating parameters. As a typical case, the measure of the refractive index in the range 1.3÷1.4 by means a spectrometer operating in visible radiation between 400 and 700 nm can be considered. Assuming that the Bragg wavelength $\lambda_c$ corresponds to the refractive index $n_c$, the following condition is obtained for the parameters $\Lambda$, $\theta_{in}$ and $\varphi$:

$$\frac{\lambda_c}{2n_0\Lambda} = \cos(\varphi - \theta_c), \quad (7)$$

wherein $$\theta = \arcsin\frac{n\sin\theta_{in}}{n_0}$$

indicates the propagation angle of the beam inside the grating for $n=n_c$.

Being fixed $\theta_{in}$ about 50÷60° and chosen $\Lambda$ on the base of the desired sensitivity, the preceding relation provides the value of the inclination angle $\varphi$ of the reticular planes that is necessary for operating in the desired wavelength range. Incidentally it should be noted that, for a sufficiently great $\Lambda$, the first member in Equation 7 tends to zero, whereby $\varphi-\theta_c$, tends to $\pi/2$. In this case the condition of maximum for $S_1$ is automatically met with a good approximation.

Figure 5:
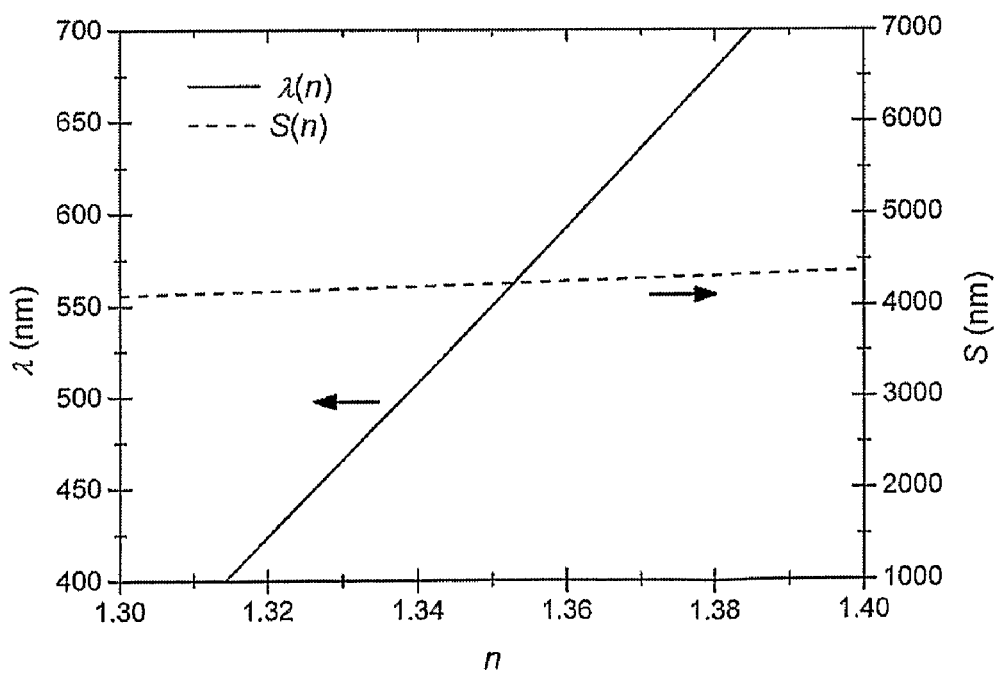
FIG. 5 is a graphic of a typical response curve of the apparatus (solid line) and the relevant sensitivity (broken line), both in ordinates, being n in abscissa.

In FIG. 5 a solid line shows a typical response curve of the apparatus, being calculated by assuming the following parameters: $\Lambda=2$ µm, $\theta_{in}=50°$, $n_0=1.49$, $\varphi=-51.3°$, the last value being chosen in order to have $\lambda_c=550$ nm for $n_c=1.35$. In the same figure the sensitivity S is represented as a broken line; it is almost constant in the considered range of refractive indices, as a result of the almost linear pattern of the response curve. This characteristic is obviously very useful in using the apparatus.

Figure 6:
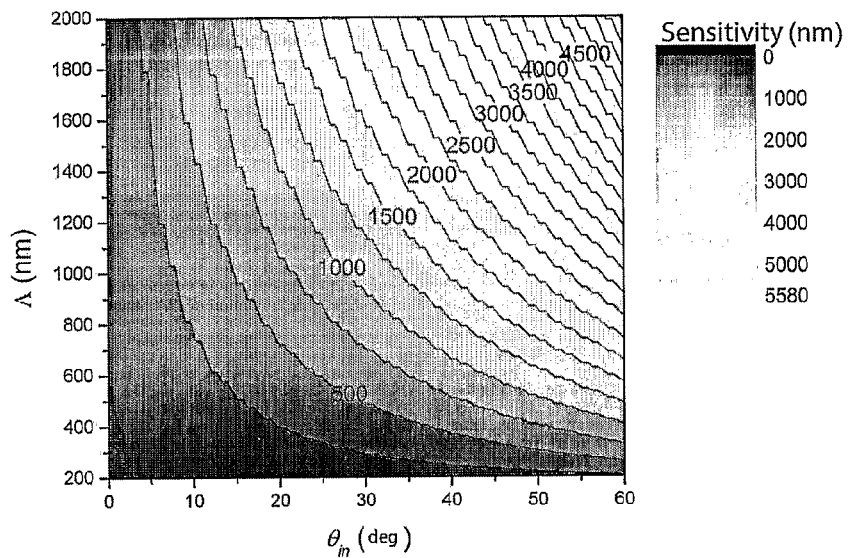
FIG. 6 is a graphic of a typical dependence of the sensitivity S on the pitch $\Lambda$ of the grating (in ordinate) and on the incidence angle $\theta_{in}$ (in abscissa) with $\phi$ being chosen point per point in such a way to meet Equation 7 for $\lambda_c=550$ nm and $n_c=1.35$.

What has been said before is summarised in the graphic of FIG. 6, in which typical values of sensitivity S are shown with $\Lambda$ and $\theta_{in}$ being variable parameters and $\varphi$ being chosen point per point so to meet Equation 7 for $\lambda_c=550$ nm and $n_c=1.35$.

For a given sensitivity S, the greatest resolution of apparatus, i.e. the variation of refractive index $\delta n$ corresponding to the lowest measurable variation of the Bragg wavelength $\delta\lambda$, is provided by $$\delta n = \frac{1}{S}\delta\lambda, \quad (8)$$

wherein the value of $\delta\lambda$ is established by the spectral resolution of the spectrometer and by the width of the diffraction peak of the grating. The commercial spectrometers typically achieve resolution in the region of 0.1 nm. However, the typical width at middle height of a Bragg diffraction grating is usually a greater order of magnitude. In fact, other parameters being equal, the spectral resolution of a Bragg diffraction grating depends on the number of periods crossed by the light in its propagation through the grating; in other words $\delta\lambda$ is as smaller as the pitch $\Lambda$ of the grating is smaller and as the thickness d of the grating is greater. This observation indicates an upper limit in the choice of the grating pitch. Bragg volume gratings of commercial kind, which are characterised by a spectral resolution $\delta\lambda \leq 1$ nm and a pitch $\Lambda$ of few microns. Thus, by considering $\delta\lambda=1$ nm and a sensitivity S=4000 nm, achievable by considering $\Lambda=2000$ nm, a resolution of the apparatus $\delta n=2.5\times 10^{-4}$ is obtained.

In the end, it is suitable to consider the measuring range $\delta n$ of the apparatus corresponding to a given operating range $\Delta\lambda$ of the spectrometer. Since the response curve of the apparatus is almost linear (constant sensitivity), it occurs approximately that $$\Delta n = \frac{1}{S}\Delta\lambda, \quad (9)$$

wherein $\Delta\lambda$ is in the region of some hundreds of nanometers for the common spectrometers.

Experimental Check of the Operation

A first prototype of the apparatus has been made and experimentally tested by utilising a grating of holographic-polymer dispersed liquid crystal (H-PDLC) as a diffraction element. H-PDLCs are Bragg holographic gratings consistent of a periodical sequence of planes of polymer and liquid crystal which are enclosed between two glasses. The grating that was used in the prototype was characterised by the following rated parameters: $n_0 \approx 1.57$, $\Lambda \approx 1$ μm, $\phi \approx 60°$; the grating has been obliquely mounted in a glass cuvette (a parallelepiped having a size of L×W×H=2.5×1.5×1.5 cm) to form an angle $\Lambda_{in} \approx 50°$ with the cuvette windows.

Figure 7:
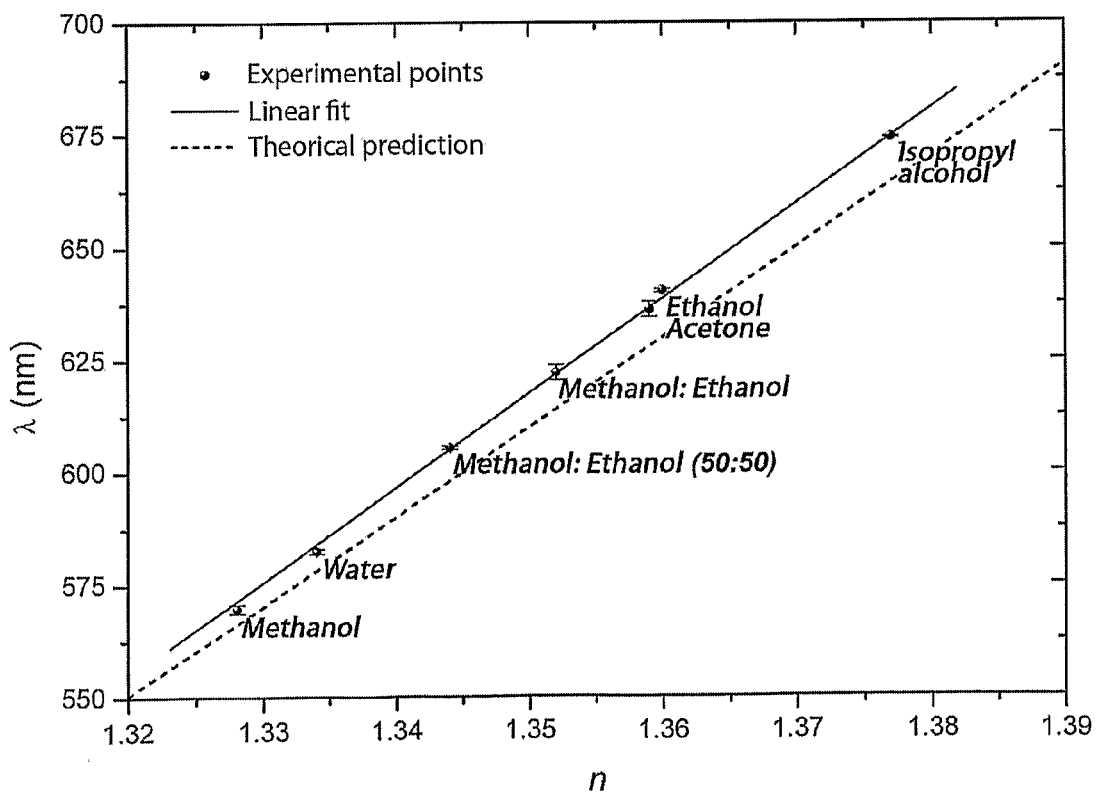
FIG. 7 is a graphic relating to an experimental check of operation of the apparatus according to the invention where experimental data are indicated by points, a linear fit by a solid line and a theoretical model by a broken line.

In order to check the operation of the apparatus, the position of the Bragg diffraction peak corresponding to a series of liquid materials having a known index has been measured. A halogenous lamp was used as a source; a high-resolution spectrometer HR4000 from Ocean Optics (resolution ~0.13 nm) was used as a spectrometer. Results, which are graphically represented in FIG. 7, are cited in following Table 1:

TABLE 1

| Material | n | λ (nm) |
|---|---|---|
| Methanol | 1.328 | 569.6 ± 0.9 |
| Water | 1.334 | 582.4 ± 0.5 |
| Methanol:Ethanol (50:50) | 1.344 | 605.3 ± 0.4 |
| Methanol:Ethanol (25:75) | 1.352 | 622.2 ± 1.6 |
| Acetone | 1.359 | 636.2 ± 1.8 |
| Ethanol | 1.360 | 640.3 ± 0.3 |
| Isopropyl alcohol | 1.377 | 674.12 ± 0.15 |

The cited values of diffracted wavelengths λ for each materials are the averages of five repeated measures with the standard deviation indicating the uncertainty; the refractive index n of each material was extracted by literature.

Some considerations can be made. The response curve is generally linear; a linear fit through experimental points (solid curve in FIG. 7) provides an angular factor (sensitivity) of 2121±8 nm, well in accordance with an expected value on the grounds of the rated parameters of the grating ($S \approx 2000$). After establishing the linear-response curve of the apparatus by means of a calibration process, the value of the refractive index can be obtained from the measured value of the diffracted wavelength through simple arithmetic operation, apart from the knowledge of the grating parameters that are often difficult to be determined with extreme precision.

By using the above mentioned parameters cited for the grating, Equation 3 provides the theoretical response curve, which is represented by a broken line in FIG. 7. The congruity with the experimental data is best, if it is considered that least changes in grating parameters give great variations in the response curve.

The uncertainty λ which is represented by error bars, i.e. the value of standard deviation on five repeated measures, is in the region of 1 nm, which corresponds to an uncertainty on n of about $5 \times 10^{-4}$. This uncertainty, which defines the accuracy of the apparatus, is a result of a multiplicity of elements, such as small misalignments of the apparatus during the measurements, mechanical instabilities, impurities growth in the cuvette, optical noise, resolution of both grating and spectrometer, etc. The most of these influences can be strongly reduced by using an improved apparatus.

The advantages of the apparatus are several. The low cost and the versatility can be considered among the main advantages. The cuvette and the grating as base components of the apparatus are extremely cheap. For these reasons this apparatus is fit to be proposed as a simple economical accessory to transform any commercial spectrometer into a high sensitivity refractometer.

Various materials can be measured. The apparatus has been developed for measuring the refractive index of fluids, including liquids, gases, emulsions, suspensions, gels, etc., but, more in general, measures of refractive index can be performed on any material, also a solid, provided that it is sufficiently transparent in the wavelength range of interest and fills the cuvette homogeneously. For example the material can be also a powder.

A typical wavelength range for the present apparatus is in near UV-visible-near IR, so that it can be used with the most commercial spectrometers. However, the operating spectral range of the apparatus can be easily shifted or scaled provided that:

the radiation source and the spectrometer are suitably chosen;

the cuvette, the grating and the material to be examined are sufficiently transparent in the pre-set spectral range;

the grating parameters (pitch and inclination angle) are chosen so that Bragg diffraction is given in the desired range.

Being the grating in a fixed position in the cuvette, the apparatus provides the value of the refractive index of the material to be examined at the diffracted wavelength. By permitting the grating to be rotated manually or electronically, the refractive index can be measured at different wavelengths.

Further, the present invention allows variations in the refractive index to be monitored in time. In this way the evolution of physical, chemical, or biological properties of a specimen, can be monitored in real time, the specimen being probably subjected to electrical, optical, and thermal influences, etc., which are suitably induced from outside.

INDUSTRIAL APPLICABILITY

The apparatus according to the invention can be used as an accessory to convert a general commercial spectrometer into a refractometer.

The cuvette can be particularly designed for its use with a specific commercial spectrometer.

The apparatus allows to measure physical, chemical, or biological properties of a material to be examined that are directly connected to the refractive index.

It can be used to measure in real time variations in the refractive index, which are probably suitably induced from outside by acting on the material to be examined chemically, electrically, thermally, optically, etc.

For example the apparatus can be used to measure the refractive index and any other physical, chemical or biological property connected thereto, in fluids flowing through the cuvette.

For example the radiation can be polarised linearly (transverse electric- or transverse magnetic-polarised) or circularly.

The radiation source and all the other optical components (cuvette, grating, and spectrometer) are chosen to operate in a particular spectral range (ultraviolet, visible, infrared or microwaves).

The material to be examined can be a fluid, i.e. liquid or aeriform, as well as a mixture of fluids, an emulsion, a suspension, a gel, etc.

The material to be examined can be a powder or other solid substance that can fill homogeneously said cuvette and is sufficiently transparent in the wavelength range of interest.

The material to be examined can be a transparent solid that is shaped in the form of two straight prismatic bodies.

The material to be examined can be a biological system, for example cellular suspensions, homogenised tissues, secretions, nutrients, etc.

The material to be examined can be partially absorbent or shedding.

The cuvette and the material therein are controlled in temperature, for example by using a Peltier cell.

The diffraction grating that is contained in the cuvette can be rotated manually or electronically in order to change the incidence angle of the radiation beam onto the grating. In this way it is possible to measure the refractive index of a given material at different wavelengths, to modify the wavelength range measurable with a given grating, and to change the sensitivities.

The invention claimed is:

1. A method for measuring the refractive index of a material with Bragg gratings, comprising an emission of a radiation from a radiation source, an interaction of the radiation with a Bragg grating, a spectral analysis of the radiation that interacted with the Bragg grating and a correlation of the spectral analysis with a value of the refractive index of the material to be examined, comprising the following steps:
  emitting a collimated radiation beam from a radiation source with a large spectrum and orientation thereof along a direction normal to the material to be examined;
  propagating the collimated radiation beam entering the material to be examined, then a Bragg diffraction grating that is obliquely placed to the direction of the collimated radiation beam, and again the material to be examined;
  subjecting to spectral analysis the collimated radiation beam exiting the material to be examined, the grating producing a minimum in the spectrum subjected to the spectral analysis in accordance with Bragg's law; and
  calculating the refractive index of the material to be examined from the measure of the wavelength corresponding to said minimum in the spectrum.

2. An apparatus for measuring the refractive index of a material with Bragg gratings, comprising:
  a radiation source able to emit a collimated radiation beam along a radiation direction;
  optical components including a spectrometer and means for calculating a refractive index;
  means for supporting to sustain the material to be examined arranged so that the radiation direction of the collimated radiation beam is normal to the material to be examined; and
  a Bragg diffraction grating placed inside the material to be examined in an oblique condition with respect to an entering radiation beam striking and crossing said Bragg diffraction grating, wherein
  the spectrometer is able to receive a radiation beam exiting the material to be examined and analyse a spectrum thereof,
  the Bragg diffraction grating produces a minimum in the spectrum subjected to spectral analysis in accordance with Bragg's law, and
  the means for calculating determines the refractive index of the material to be examined from a measure of the wavelength corresponding to said minimum in the spectrum.

3. The apparatus according to claim 2, wherein the collimated radiation beam is linearly polarised.

4. The apparatus according to claim 3, wherein the collimated radiation beam is linearly polarised along a polarisation chosen between a transverse electric polarisation and a transverse magnetic polarisation.

5. The apparatus according to claim 2, wherein the collimated radiation beam is circularly polarised.

6. The apparatus according to claim 2, wherein said radiation beam source and the optical components are chosen to operate in a particular spectral range that is chosen among ultraviolet, visible, infrared and microwaves.

7. The apparatus according to claim 2, wherein the means for supporting to sustain the material to be examined comprises rigid supporting elements, and the material to be examined is a transparent solid material.

8. The apparatus according to claim 7, wherein the transparent solid material is shaped in a couple of prismatic bodies having opposed faces which are complementary inclined, between which the Bragg diffraction grating is interposed similarly inclined.

9. The apparatus according to claim 2, wherein the means for supporting to sustain the material to be examined comprises a cuvette inside the Bragg diffraction grating and having parallel transparent opposed walls that are arranged perpendicularly to the collimated radiation beam.

10. The apparatus according to claim 9, wherein the material to be examined is a material in any physical state such that it can be contained in a cuvette.

11. The apparatus according to claim 2, wherein the means for supporting to sustain the material to be examined comprises a sealable cuvette containing inside the Bragg diffraction grating and having parallel transparent opposed walls that are arranged perpendicularly to the collimated radiation beam.

12. The apparatus according to claim 11, wherein the material to be examined is aeriform.

13. The apparatus according to claim 9, wherein the Bragg diffraction grating is tiltable in a controlled manner to change an incidence angle of the radiation beam onto the same.

14. The apparatus according to claim 2, wherein the means for supporting to sustain the material to be examined is a standard cuvette in its kind and size, which is adapted to contain the Bragg diffraction grating and then usable with all commercial spectrophotometers.

15. The apparatus according to claim 10, wherein the Bragg diffraction grating is tiltable in a controlled manner to change an incidence angle of the radiation beam onto the same.

16. The apparatus according to claim 11, wherein the Bragg diffraction grating is tiltable in a controlled manner to change an incidence angle of the radiation beam onto the same.

17. The apparatus according to claim 12, wherein the Bragg diffraction grating is tiltable in a controlled manner to change an incidence angle of the radiation beam onto the same.

18. The method according to claim 1, wherein a response curve is a pattern of wavelength λ diffracted by the Bragg grating in dependence on the refractive index n of the material to be examined:

$$\lambda = 2n_0 \Lambda \cos\left[\varphi - \arcsin\left(\frac{n \sin\theta_{in}}{n_0}\right)\right]$$

where θ is a propagation angle of the beam inside the Bragg grating, Λ is the pitch of the grating 3 and φ the inclination angle of reticular planes of the Bragg grating.

19. The apparatus according to claim 2, wherein a response curve of the apparatus is a pattern of wavelength λ diffracted by the Bragg grating in dependence on the refractive index n of the material to be examined:

$$\lambda = 2n_0 \Lambda \cos\left[\varphi - \arcsin\left(\frac{n\sin\theta_{in}}{n_0}\right)\right]$$

where θ is a propagation angle of the beam inside the Bragg grating, Λ is the pitch of the grating 3 and φ the inclination angle of reticular planes of the Bragg grating.

20. An apparatus for measuring the refractive index of a material to be examined, comprising:

a radiation source able to emit a collimated radiation beam along a radiation direction;

a support configured to sustain the material to be examined arranged so that the radiation direction of the collimated radiation beam is normal to the material to be examined;

a Bragg diffraction grating placed inside the material to be examined in an oblique condition with respect to an entering radiation beam striking and crossing said Bragg diffraction grating; and a spectrometer configured to receive a radiation beam exiting the material to be examined and analyse a spectrum thereof, wherein the Bragg diffraction grating produces a minimum in the spectrum subjected to spectral analysis in accordance with Bragg's law, and a calculator determines the refractive index of the material to be examined from a measure of the wavelength corresponding to said minimum in the spectrum.

* * * * *